United States Patent
Shimizu

(10) Patent No.: US 9,351,637 B2
(45) Date of Patent: May 31, 2016

(54) CORNEA SHAPE MEASUREMENT APPARATUS

(75) Inventor: Kazunari Shimizu, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 152 days.

(21) Appl. No.: 13/976,750

(22) PCT Filed: Dec. 20, 2011

(86) PCT No.: PCT/JP2011/079562
§ 371 (c)(1),
(2), (4) Date: Jun. 27, 2013

(87) PCT Pub. No.: WO2012/090796
PCT Pub. Date: Jul. 5, 2012

(65) Prior Publication Data
US 2013/0286351 A1    Oct. 31, 2013

(30) Foreign Application Priority Data
Dec. 27, 2010  (JP) .................................. 2010-291223

(51) Int. Cl.
*A61B 3/10*    (2006.01)
*A61B 3/107*    (2006.01)
(Continued)

(52) U.S. Cl.
CPC .................. *A61B 3/107* (2013.01); *A61B 5/107* (2013.01); *A61B 5/103* (2013.01)

(58) Field of Classification Search
CPC .......... A61B 3/107; A61B 3/158; A61B 3/10; A61B 3/14; A61B 3/0025; A61B 3/0058; A61B 3/1005; A61B 3/1015; A61B 3/1025; A61B 5/103; A61B 5/107; G01B 11/25; G01B 11/24; G01B 11/255; G01B 11/2513
USPC .................. 351/211, 212, 205, 206, 221, 246
See application file for complete search history.

(56) References Cited

U.S. PATENT DOCUMENTS 5,159,361 A * 10/1992 Cambier et al. ............... 351/212
5,835,190 A * 11/1998 Miyake .................. A61B 3/107
351/212
(Continued)

FOREIGN PATENT DOCUMENTS

| EP | 2000079 A1 | 12/2008 |
|---|---|---|
| JP | 04-150831 | 5/1992 |

(Continued)

OTHER PUBLICATIONS

International Search Report corresponding to PCT/JP2011/079562, dated Jan. 24, 2012.

*Primary Examiner* — Bumsuk Won
*Assistant Examiner* — Collin X Beatty
(74) *Attorney, Agent, or Firm* — Rankin, Hill & Clark LLP

(57) ABSTRACT

A cornea shape measurement apparatus includes: a first projecting optical system configured to project a first target on the cornea; a first imaging optical system configured to capture a reflection image of the first target projected on the cornea; a second projecting optical system configured to project a second target different from the first target on the cornea to measure a corneal shape; a second imaging optical system configured to capture a reflection image of the second target projected on the cornea; and a calculation controller configured to adjust the amount of projection light of the second projecting optical system based on the reflection image of the first target, the reflection image having been acquired by the first imaging optical system, and measuring the corneal shape of an examinee's eye based on the reflection image of the second target, the reflection image having been captured by the imaging optical system.

12 Claims, 2 Drawing Sheets

(51) Int. Cl.
*A61B 5/107* (2006.01)
*A61B 5/103* (2006.01)

(56) References Cited

U.S. PATENT DOCUMENTS

| | | | |
|---|---|---|---|
| 5,873,832 A * | 2/1999 | Maloney et al. | 600/473 |
| 5,907,388 A | 5/1999 | Fujieda | |
| 6,007,204 A * | 12/1999 | Fahrenkrug et al. | 351/221 |
| 6,024,449 A * | 2/2000 | Smith | A61B 3/107 351/212 |
| 6,152,565 A * | 11/2000 | Liu et al. | 351/212 |
| 6,234,631 B1 * | 5/2001 | Sarver et al. | 351/212 |
| 6,234,978 B1 | 5/2001 | Mihashi et al. | |
| 6,447,119 B1 * | 9/2002 | Stewart et al. | 351/212 |
| 6,497,483 B2 * | 12/2002 | Frey et al. | 351/212 |
| 6,540,692 B2 | 4/2003 | Mihashi et al. | |
| 6,609,794 B2 * | 8/2003 | Levine | 351/221 |
| 6,755,528 B2 | 6/2004 | Isogai | |
| 6,779,891 B1 * | 8/2004 | Barth et al. | 351/212 |
| 7,458,683 B2 * | 12/2008 | Chernyak | 351/205 |
| 2003/0107708 A1 * | 6/2003 | Isogai | G01B 11/25 351/200 |
| 2004/0189936 A1 * | 9/2004 | Mimura et al. | 351/205 |
| 2007/0236701 A1 * | 10/2007 | Neal et al. | 356/512 |
| 2008/0239239 A1 * | 10/2008 | Honda | 351/208 |
| 2008/0297722 A1 * | 12/2008 | Honda | 351/208 |
| 2009/0036879 A1 * | 2/2009 | Dai | A61F 9/008 606/5 |
| 2009/0128778 A1 * | 5/2009 | Honda et al. | 351/245 |
| 2011/0273669 A1 * | 11/2011 | Abitbol | A61B 3/1015 351/212 |
| 2012/0057130 A1 | 3/2012 | Naito | |
| 2012/0086911 A1 * | 4/2012 | Takii et al. | 351/208 |
| 2012/0188508 A1 * | 7/2012 | Kim et al. | 351/206 |
| 2012/0215155 A1 * | 8/2012 | Muller et al. | 604/20 |
| 2013/0278898 A1 * | 10/2013 | Kato | 351/208 |
| 2013/0286350 A1 * | 10/2013 | Sakashita et al. | 351/208 |
| 2013/0286351 A1 * | 10/2013 | Shimizu | 351/212 |
| 2014/0268044 A1 * | 9/2014 | Copland | 351/206 |
| 2014/0320815 A1 * | 10/2014 | Steinmueller | 351/206 |

FOREIGN PATENT DOCUMENTS

| | | |
|---|---|---|
| JP | 10-108837 A | 4/1998 |
| JP | 10-216092 A | 8/1998 |
| JP | 2003-169778 A | 6/2003 |
| JP | 2005-137662 | 6/2005 |
| JP | 2005-137662 A | 6/2005 |
| JP | 2006-34744 A | 2/2006 |
| JP | 2007-215950 A | 8/2007 |
| JP | 2008-295972 | 12/2008 |
| JP | 2008-295972 A | 12/2008 |
| JP | 2010-252994 A | 11/2010 |
| WO | 2010122973 A1 | 10/2010 |

* cited by examiner

CORNEA SHAPE MEASUREMENT APPARATUS

RELATED APPLICATIONS

The present application is a National Phase of International Application Number PCT/JP2011/079562, filed Dec. 20, 2011, and claims priority from Japanese Application Number 2010-291223, filed Dec. 27, 2010.

TECHNICAL FIELD

The present invention relates to a cornea shape measurement apparatus that measures a corneal shape of an examinee's eye.

BACKGROUND ART

A cornea shape measurement apparatus includes, for example, an optical system that projects a target pattern on the cornea, an optical system that takes the projected target pattern image, and a calculation unit that performs corneal topographic calculation by analyzing the captured pattern image (see Patent Document 1).

CITATION LIST

Patent Document

Patent Document 1: JP-A-2007-215950

SUMMARY OF THE INVENTION

Problems to be Solved by the Invention

The above apparatus monitors a variation in luminance of the captured target pattern, and acquires as a pattern for analysis the target pattern image in which the necessary luminance for measurement is ensured. In other words, the above apparatus projects the same target pattern on the cornea several times.

In view of the above conventional technique, a technical problem of the present invention is to provide a cornea shape measurement apparatus that can acquire a measurement result with a low burden on an examinee and with high accuracy.

Solutions to the Problems

In order to solve the above problem, the present invention has the following features.

(1) A cornea shape measurement apparatus for measuring a corneal shape of an examinee's eye includes:
a first projecting optical system configured to project a first target on the cornea;
a first imaging optical system configured to capture a reflection image of the first target projected on the cornea;
a second projecting optical system configured to project a second target different from the first target on the cornea to measure the corneal shape;
a second imaging optical system configured to capture a reflection image of the second target projected on the cornea; and
a calculation controller configured to adjust the amount of projection light of the second projecting optical system based on the reflection image of the first target, the reflection image having been acquired by the first imaging optical system, and measuring the corneal shape of the examinee's eye based on the reflection image of the second target, the reflection image having been captured by the second imaging optical system.

(2) The cornea shape measurement apparatus of (1), wherein
the first projecting optical system comprises an infrared light source, and projects the first target on the cornea with infrared light, and
the second projecting optical system comprises a visible light source, and projects the second target on the cornea with visible light.

(3) The cornea shape measurement apparatus of (1) or (2), wherein the second projecting optical system projects a target having a wider projection area on the cornea than the first target as the second target on the cornea.

(4) The cornea shape measurement apparatus of any one of (1) to (3), wherein the calculation controller has:
measuring a first corneal shape of the examinee's eye based on the reflection image of the first target, the reflection image having been captured by the first imaging optical system;
adjusting the amount of projection light of the second projecting optical system based on the first corneal shape; and
measuring a second corneal shape of the examinee's eye based on the reflection image of the second target, the reflection image having been captured by the second imaging optical system.

(5) The cornea shape measurement apparatus of any one of (1) to (4), wherein the first imaging optical system serves also as the second imaging optical system.

Effects of the Invention

According to the present invention, a burden on an examinee can be reduced, and an accurate measurement result can be acquired.

DESCRIPTION OF EMBODIMENTS

An embodiment of the present invention will be described with reference to the drawings. FIG. 1 is a diagram schematically illustrating the configuration of a cornea shape measurement apparatus according to the embodiment. FIG. 2 is an exemplary diagram illustrating a first target image and an anterior segment image, which have been captured by an imaging optical system, and illustrating a state of a monitor displaying a captured image. FIG. 3 is an exemplary diagram illustrating a second target image and an anterior segment image, which have been captured by an imaging optical system. FIG. 4 is a diagram illustrating a method for measuring a corneal shape using a first target pattern image.

The present apparatus will be briefly described. The cornea shape measurement apparatus includes a first projecting optical system 1, a second projecting optical system 10, an imaging optical system 20, and a calculation control unit 70. The cornea shape measurement apparatus measures the distribution of a corneal shape of an examinee's eye E. The configurations of the respective systems 1, 10, and 20 and the unit 70 are not limited to those illustrated in FIG. 1.

The first projecting optical system 1 projects a first target on a cornea Ec (see, for example, a target T2 in FIG. 2). The first projecting optical system 1 is used, for example, to measure a corneal shape simply. It is preferable that the light forming a pattern of the first target be light that places a low burden on the eye, for example, infrared light (or near-infrared light) that is not dazzling to the eye. Moreover, even if it is visible light, as long as it is a target pattern where the projection area on the cornea is limited to a part, a certain effect can be obtained. The first target pattern may be, for example, a target for measuring a corneal curvature (curvature radius) of a part on the cornea.

The first projecting optical system 1 includes, for example, a light source arranged at a position away from an optical axis L1 of the imaging optical system 20, and projects a target toward the cornea Ec in the oblique direction. The first projecting optical system 1 projects, for example, a point target, a ring target, a slit target, or the like on the cornea Ec. The light source may be one or more in number. The light source may be a point light source, a ring light source, or a slit light source. It is preferable that an infrared light source or a visible light source be used as the light source.

The first projecting optical system 1 may be a dedicated optical system, or may also serve as an optical system used for another purpose. In the case of using it for dual purposes, for example, an alignment optical system is used as the first projecting optical system.

The second projecting optical system 10 projects a second target different from the first target on the cornea Ec (see, for example, FIG. 3). The second target and the first target are different, for example, in at least either of a projection area and a wavelength used. The second projecting optical system 10 is used to measure the distribution of a corneal shape. It is preferable that a pattern of the second target be a pattern that can measure a corneal shape over a wide area. For example, with regard to the projection area on the cornea, the second target pattern is wider than the first target pattern.

The second projecting optical system 10 includes, for example, a light source arranged at a position away from the optical axis L1, and projects a target toward the cornea Ec in an oblique direction. The second projecting optical system 10 projects, for example, a point target, a ring target, a slit target, or the like on the cornea Ec. More preferably, the second projecting optical system 10 projects a plurality of ring patterns or grid patterns to project a target in a wide area of the cornea. The light source may be one or more in number. Moreover, the light source may be a point light source, a ring light source, or a slit light source.

A visible light source or an infrared light source is used as the light source. For example, visible light (for example, blue, green, or red) is used as the second target pattern. Especially, the use of blue light is effective to avoid the influence of brown and black irises. The wavelengths of the visible light are usually set to $\lambda = 360$ nm to 830 nm.

The configurations of the first projecting optical system 1 and the configuration of the second projecting optical system 10 may partially overlap each other. For example, the second projecting optical system 10 may be an optical system that projects multiple ring patterns. It may be configured such that the ring pattern of part of the second projecting optical system 10 is used as the first projecting optical system 1.

The imaging optical system 20 includes an imaging device 22 and captures reflection images of the first and second targets projected on the cornea. The imaging device 22 is arranged, for example, at a position substantially conjugated with the anterior segment. In the imaging optical system 20, the wavelength band where an image can be captured is set in accordance with the wavelength bands of the first projecting optical system 1 and the second projecting optical system 10. For example, a two-dimensional light receiving device such as a two-dimensional CCD or a two-dimensional CMOS is used as the imaging device 22. The imaging optical system 20 may capture an anterior segment image in addition to capturing of a target pattern. The output of the imaging device 22 is connected to the calculation control unit 70.

The imaging device and imaging optical system for capturing the first target may preferably have the same configurations as the imaging device and imaging optical system for capturing the second target, respectively. However, for example, the imaging optical systems may be different from each other. In FIG. 1, the imaging optical system that captures the first target also serves as the imaging optical system that captures the second target.

The calculation control unit 70 is configured, for example, of a CPU and controls the configurations. The calculation control unit 70 measures a corneal shape based on a reflection image of a target, the reflection image having been captured by the imaging device 22. The calculation control unit 70 adjusts the amount of projection light of the second projecting optical system 10 based on the reflection image of the first target. The calculation control unit 70 measures the corneal shape of the eye E based on the reflection image of the second target.

For example, the calculation control unit 70 uses the first projecting optical system 1 to project the first target pattern on the cornea. The calculation control unit 70 measures the corneal shape based on the first target pattern image projected on the cornea. Next, the calculation control unit 70 uses the second target projecting optical system 10 to project the second target pattern on the cornea. The calculation control unit 70 acquires the second target pattern image projected on the cornea by the imaging optical system 20. The calculation control unit 70 acquires the second target pattern image as a pattern for analysis and then stores the second target pattern image in a storage unit 72. It is preferable that the projection of the second target pattern be ended immediately after the pattern for analysis is acquired.

At this point, the calculation control unit 70 controls the amount of light of the second target pattern based on the corneal shape acquired by the first target pattern (the first measurement result). The reason why the amount of light of the second target pattern is changed in accordance with the corneal shape is to ensure the necessary amount of light for measurement. In other words, the smaller the corneal curvature radius, the more the reflected light of the target pattern from the cornea is facilitated to advance toward the periphery of the eye to reduce the amount of light heading for the imaging optical system. As a consequence, it tends to cause a shortage of light. On the other hand, the larger the corneal curvature radius, the more the reflected light of the target pattern from the cornea is facilitated to reflect in the front direction to increase the amount of light heading for the imaging optical system.

Therefore, the second target pattern is projected with the amount of light appropriate to the corneal curvature of the eye E in accordance with the result of capturing the first target pattern. The amount of light of a target pattern may be set high from the beginning regardless of the corneal curvature. However, this is not necessarily a good method considering the burden on the eye. The projection of the target pattern places a burden on an examinee (for example, in the case of visible light, there is a problem of glare).

For example, the calculation control unit 70 determines whether or not a first result obtained by the first target pattern satisfies a predetermined threshold, and controls the amount of light based on the determination result. At this point, if the first result is larger than a predetermined corneal curvature radius, the calculation control unit 70 adjusts the amount of projection light such that the second target pattern is projected at a first light amount level. Moreover, if the first result is equal to or less than the predetermined corneal curvature radius, the calculation control unit 70 adjusts the amount of projection light such that the second target pattern is projected at a second light amount level larger than the first light amount level.

In the method for adjusting the amount of light, the voltage to be applied to the light source may be controlled or the amount of light may be controlled by a filter arranged between the light source and the eye (for example, a liquid crystal shutter). The calculation control unit 70 does not need to change all the amount of light of the second target pattern. The calculation control unit 70 may change the amount of light, for example, for the periphery of the second target pattern.

The calculation control unit 70 analyzes the second target pattern image stored in the storage unit 72, and acquires distribution information on the corneal shape of the eye E. The calculation control unit 70 then outputs the obtained distribution information as numeric values and a color map. The obtained distribution information is used for the selection of an intraocular lens, refractive laser surgery, and the like.

The present apparatus uses the simple first target pattern to measure a corneal shape. The corneal shape measured simply is then used to adjust the amount of light of the second target pattern used for corneal analysis. With the analysis of the second target pattern image, the corneal shape is measured in a wide area, and the measurement result is outputted. Consequently, measurement accuracy can be ensured. Furthermore, only small light emission amount of the second target pattern, which is a heavy burden on the eye, is necessary. Therefore, the burden on the examinee is reduced.

It is preferable that the apparatus project the second target pattern image immediately after the measurement of the first corneal curvature. Consequently, the second target pattern used for corneal analysis is acquired in a short time. Reduction in measurement accuracy accompanied by reduction in tears is avoided.

Moreover, the apparatus projects the first target pattern on the cornea with infrared light, and projects the second target pattern on the cornea with visible light. Consequently, the burden on the eye at the time of simple measurement is further reduced.

If the amount of projection light of the second projecting optical system 10 is adjusted based on the reflection image of the first target, the calculation control unit 70 is not limited to the method using a corneal shape measured based on the reflection image of the first target. The calculation control unit 70 uses the result of capturing the reflection image of the first target. For example, the calculation control unit 70 detects a light amount level of the reflection image of the first target. The calculation control unit 70 adjusts the amount of projection light of the second projecting optical system 10 based on the detected light amount level. In this case, as the light amount level of the first target is lower, the amount of projection light of the second target is increased.

Hereinafter, an example of the cornea shape measurement apparatus according to the embodiment will be described in detail. In this case, a projecting optical system 45a is used as an example of the first projecting optical system 1. The projecting optical system 45a projects a target for detecting an alignment state in a Z direction with respect to the eye E. A placido target projecting optical system 11 is used as an example of the second projecting optical system 10. Moreover, an anterior segment observing optical system 21 is used as the imaging optical system 20.

The optical systems of the apparatus according to the example are broadly divided into the placido target projecting optical system 11, the imaging optical system 20, a fixation target presenting optical system 30 for fixating the examinee's eye, an X-Y alignment target projecting optical system 40, a working distance detecting optical system 45 (the projecting optical system 45a and a detecting optical system 45b), and an eye refractive power distribution measuring optical system 9. The placido target projecting optical system 11 projects a placido target on the cornea of the examinee's eye. The imaging optical system 20 captures the anterior segment of the examinee's eye. The X-Y alignment target projecting optical system 40 projects a target for alignment in the X and Y directions (up, down, left, and right) on the cornea of the examinee's eye. The working distance detecting optical system 45 projects a target for alignment in the Z direction (working distance) on the cornea of the examinee's eye, and detects its reflected light. Consequently, the working distance detecting optical system 45 detects alignment information in the Z direction of the apparatus main body with respect to the examinee's eye. The eye refractive power distribution measuring optical system 9 measures the eye refractive power distribution or wavefront aberration of the examinee's eye. These optical systems are arranged in an unillustrated housing. The housing is moved three-dimensionally with respect to the eye E by a known alignment shifting mechanism.

Firstly, the placido projecting optical system 10 will be described. A placido plate 12 has a substantially hemispherical shape and has an opening at the center thereof. The placido plate 12 has a ring pattern having multiple light transmitting parts and light shielding parts that form concentric circles around an optical axis L1. A visible light source 13 emits visible light such as an LED. The light emitted from the light source 13 is reflected by a reflective plate 14, and illuminates the placido plate 12 substantially uniformly from behind. A placido ring image is projected on the cornea of the examinee's eye. An anterior segment illuminating light source 15 is arranged on the periphery of the placido plate 12, and illuminates the anterior segment with near-infrared light.

Moreover, the target projecting optical system 45a and the target detecting optical system 45b are symmetrically arranged right and left about the optical axis L1 behind the reflective plate 14. The target projecting optical system 45a includes an infrared light source 46 and a lens 47. The target projecting optical system 45a projects a target in an oblique direction with respect to the optical axis L1. The target detecting optical system 45b includes a lens 48 and a position sensitive detector 49. The target detecting optical system 45b detects the projected target in the opposite direction.

The light flux of the target image formed on the cornea by the target projecting optical system 45a passes through the openings provided to the placido plate 12 and the reflective plate 14. Furthermore, the light flux is incident on the position sensitive detector 49 through the lens 48 of the target detecting optical system 45b. The eye E's information on alignment in the working distance direction with respect to the apparatus is detected from the position of the target image incident on the position sensitive detector 49.

A beam splitter 25 is coaxial with the optical axis L1 and an optical axis L2. The fixation target presenting optical system 30 is arranged on the optical axis L2. The fixation target presenting optical system 30 includes, for example, a visible illuminating light source 31, a fixation target 32, and a lens 33. The light source 31 illuminates the fixation target 32. The light from the fixation target 32 is projected through the lens 33, a dichroic mirror 27, a half mirror 26, an objective lens 23, and the beam splitter 25 to the fundus of the examinee's eye. The light source 31 and the fixation target 32 are movable in the optical axis L2 direction. The light source 31 and the fixation target 32 change the diopter scale of the fixation target 32 that the examinee's eye is caused to fixate, and fogs the examinee's eye.

The dichroic mirror 27 transmits visible light and reflects infrared light. The dichroic mirror 27 is coaxial with the optical axis L2 and an optical axis L3. The X-Y alignment target projecting optical system 40 is arranged on the optical axis L3. The projecting optical system 40 includes, for example, a light source 41 and a lens 42. The light from the light source 41 is reflected by the dichroic mirror 27 through the lens 42. The light is subsequently projected through the above-mentioned optical path similar to the light from the fixation target 32 to the cornea of the examinee's eye.

The half mirror 26 is coaxial with the optical axis L2 and an optical axis L4. The imaging optical system 20 is arranged on the optical axis L4. The observing optical system 21 includes the beam splitter 25, the objective lens 23, the half mirror 26, a telecentric diaphragm 24, an imaging lens 28, and the two-dimensional imaging device 22. The light flux from the anterior segment of the examinee's eye is captured (received) by the imaging device 22 through the beam splitter 25, the objective lens 23, the beam splitter 26, the imaging lens 28, and the telecentric diaphragm 24. The observing optical system 21 includes the telecentric diaphragm 24, and configures a telecentric optical system that captures a light flux parallel with the optical axis. The imaging device 22 is used to observe a front image of the anterior segment of the examinee's eye. Furthermore, the imaging device 22 is also used to capture a placido target projected on the cornea, and to detect an alignment target image formed by the light source 41.

The eye refractive power distribution measuring optical system 9 is arranged in a transmission direction of the beam splitter 25. The measuring optical system 9 includes a projecting optical system 2, a light receiving optical system 3, a beam splitter 4, and an objective lens 6. The projecting optical system 2 projects a measurement target on the fundus of the examinee's eye. The light receiving optical system 3 receives the reflected light from the fundus, which has been projected by the projecting optical system 2. The beam splitter 4 reflects the measurement light emitted from the projecting optical system 2 to cause the light to head toward the examinee's eye. The beam splitter 4 transmits the measurement light reflected by the fundus and causes the light to head toward the light receiving optical system 3. A phase difference method (see, for example, JP-A-10-108837) and a method using a Hartmann plate (see, for example, JP-A-10-216092) are conceivable as an optical system for measuring the eye refractive power distribution of the examinee's eye.

Next, a control system will be described. The calculation control unit (hereinafter controller) 70 acquires corneal shape data (corneal curvature distribution data) based on an imaging signal from the imaging device 22. The controller 70 acquires eye refractive power distribution data (wavefront aberration data) of the eye E based on a light receiving signal from the light receiving optical system 3. If a target formed by the light source 41 on the cornea is detected by the imaging device 22, the controller 70 obtains the coordinate position of the target image and detects alignment information in the X and Y directions. The controller 70 detects alignment information in the Z direction by a signal from the position sensitive detector 49.

A monitor 75 is connected to the controller 70 and displays an anterior segment image that is captured by the imaging device 22 and acquisition results such as the corneal shape data. The controller 70 controls the display of the monitor 75, and displays a color map based on the acquired corneal shape data and eye refractive power distribution data. A memory 72 as a storage means stores therein eye optical characteristics information (for example, the corneal shape information and the eye refractive power distribution information) containing the acquired mapping image and numeric value information. The controller 70 is connected to a joystick 5 for allowing an examiner to perform alignment work. A measurement start switch 5a is provided at the top of the joystick 5.

The performance of the apparatus configured as described above will be described. Firstly, the examiner makes the face of the examinee to be held on an unillustrated face support unit. The examiner subsequently uses the joystick 5 to perform alignment with the examinee's eye. The examiner performs alignment while watching an anterior segment image displayed on the display monitor 75.

FIG. 2 is a view illustrating an anterior segment observation screen upon the completion of alignment. A target T1 is a target formed by the projecting optical system 40 on the cornea. The target T2 is a target formed by the target projecting optical system 45a on the cornea. A reticle LT is an alignment reference and is electronically displayed.

The examiner moves the apparatus main body in the X and Y directions such that the target T1 is within the reticle LT. Next, the examiner moves the apparatus main body in the Z direction such that an unillustrated indicator indicates the completion of alignment.

If the alignment in the up, down, left and right directions and the working distance direction falls in an appropriate state, the examiner presses the measurement start switch 5a. The controller 70 may emit a trigger automatically for the start of measurement when the alignment information in the X, Y, and Z directions is within an allowable range.

The target T1 is a target formed by light projected on the eye E from the front direction. Upon the completion of alignment, the target T1 is arranged on the imaging optical axis L4.

After being reflected by the cornea of the eye E, part of the reflected light from the cornea of the light irradiated by the projecting optical system 45a is detected by the detecting optical system 45b. Consequently, the alignment state in the Z direction is detected.

Part (a light flux parallel with the optical axis L1) of the reflected light from the cornea of the light irradiated by the projecting optical system 45a is received by the imaging device 22 (see FIG. 4). The target T2 is a target formed by the projecting optical system 45a. The light of the target T2 is received at a position away from the optical axis L4 on the imaging device 22 upon the completion of alignment. At this point, an image height D of the target T2 with respect to the optical axis L4 varies depending on the corneal curvature radius of the eye E (see FIGS. 2 and 4).

<First Measurement>

Therefore, the controller 70 detects by image processing the coordinate position of the target T2 on a captured image output from the imaging device 22, and measures the image height D (see FIG. 2). The controller 70 may determine the distance between the imaging optical axis L4 and the target T2 as the image height D. The controller 70 may determine the distance between the target T1 and the target T2 as the image height D. The controller 70 then determines the radius of curvature based on the measured image height D. In this case, for example, a model eye having a different radius of curvature is used to previously obtain the relationship between the radius of curvature and the distance D (calibration).

The controller 70 then determines whether or not the measured radius of curvature is larger than a predetermined radius of curvature (for example, 5 mm). The determination result is used to adjust the amount of projection light of the projecting optical system 11 in a second measurement. At this point, as the radius of curvature is larger, the amount of projection light is set smaller. On the other hand, as the radius of curvature is smaller, the amount of projection light is set larger. With regard to the setting of the amount of light, the setting of the amount of light in two stages with the predetermined radius of curvature as a threshold value is illustrated, but is not limited to this. For example, it may be configured such that the amount of light can be set in three or more stages in accordance with the radius of curvature.

It is preferable that the controller 70 use an anterior segment image when alignment is determined to be complete (an image being a trigger for the start of measurement), or an anterior segment image acquired at a next frame rate of a frame rate when alignment is determined to be complete, as an anterior segment image on which the first measurement is performed.

Moreover, the corneal curvature obtained by the first measurement is used to set the amount of light. Therefore, the controller 70 may adjust the amount of light of the projecting optical system 10 in accordance with the image height D, which is in a paired relationship with the radius of curvature.
<Second Measurement>

After the end of the first measurement, the controller 70 causes the light sources of the projecting optical system 11 to emit light, and projects a placido target P on the cornea Ec (see FIG. 3). At this point, the controller 70 adjusts the applied voltage to the light source 46 in accordance with the radius of curvature acquired by the first measurement. Consequently, the controller 70 adjusts the amount of light of the placido target.

The controller 70 then captures an anterior segment image on which the placido target has been projected, using the imaging device 22. When the capturing of the anterior segment image is complete, the controller 70 obtains the distribution information of the corneal shape by the analysis of the acquired placido target. The controller 70 then displays the acquired distribution information by a color map.

In the above configuration, the projecting optical system for forming the alignment target T1 on the cornea (the projecting optical system 40) is specially provided. However, the projecting optical system 2 may serve also as this.

Moreover, the eye refractive power measurement apparatus of the embodiment may be represented as the following first to fifth cornea shape measurement apparatuses.

The first cornea shape measurement apparatus includes a first projecting optical system configured to project a first target on the cornea, a first imaging optical system configured to capture a reflection image of the first target projected on the cornea, a second projecting optical system configured to project a second target different from the first target on the cornea to measure a corneal shape, a second imaging optical system configured to capture a reflection image of the second target projected on the cornea, and a corneal shape measuring means for adjusting the amount of projection light of the second projecting optical system based on the reflection image of the first target, the reflection image having been acquired by the first imaging optical system, and measuring the corneal shape of an examinee's eye based on the reflection image of the second target, the reflection image have been captured by the second imaging optical system.

The second cornea shape measurement apparatus is the first cornea shape measurement apparatus where the first projecting optical system has an infrared light source and projects the first target on the cornea with infrared light, and the second projecting optical system has a visible light source and projects the second target on the cornea with visible light.

The third cornea shape measurement apparatus is any one of the first and second cornea shape measurement apparatuses where the second projecting optical system projects a target whose projection area on the cornea is wider than the first target, as the second target on the cornea.

The fourth cornea shape measurement apparatus is any one of the first to third cornea shape measurement apparatuses where the corneal shape measuring means has a first corneal shape measuring means for measuring the corneal shape of the examinee's eye based on the reflection image of the first target, the reflection image having been captured by the first imaging optical system, and a second corneal shape measuring means for adjusting the amount of projection light of the second projecting optical system based on the corneal shape acquired by the first corneal shape measuring means, and measuring the corneal shape of the examinee's eye based on the reflection image of the second target, the reflection image having been captured by the second imaging optical system.

The fifth cornea shape measurement apparatus is any one of the first to fourth cornea shape measurement apparatuses where the first imaging optical system serves also as the second imaging optical system.

Figure 1:
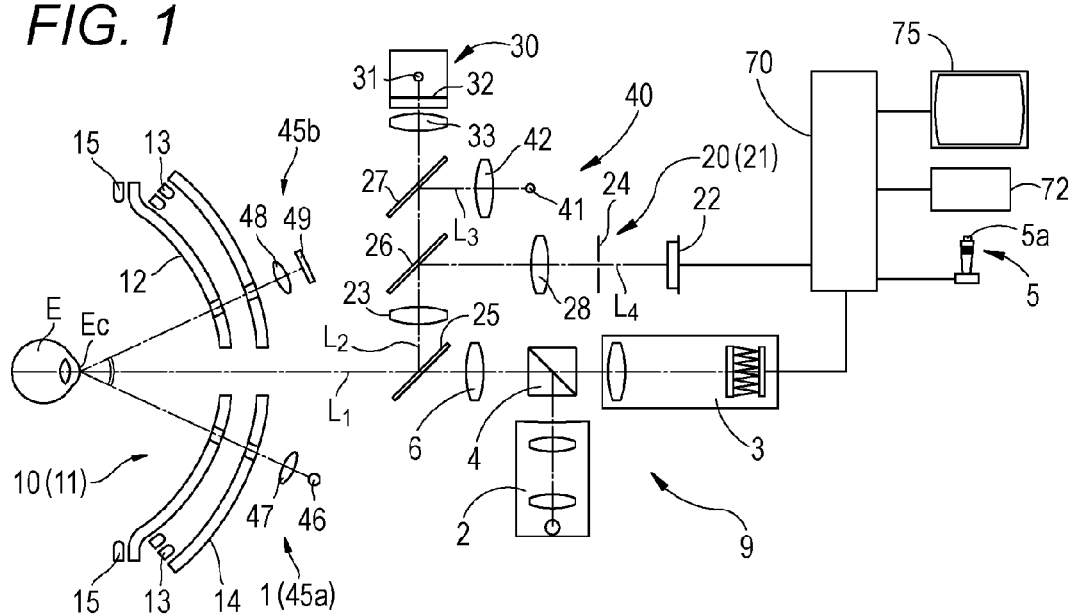
FIG. 1 is a diagram schematically illustrating the configuration of a cornea shape measurement apparatus according to the embodiment.
Figure 2:
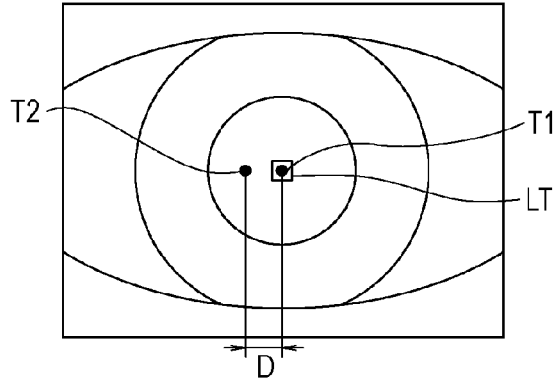
FIG. 2 is an exemplary diagram illustrating a first target image and an anterior segment image, which have been captured by an imaging optical system, and illustrating a state of a monitor displaying a captured image.
Figure 3:
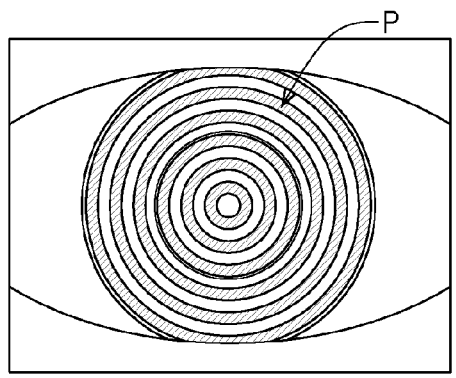
FIG. 3 is an exemplary diagram illustrating a second target image and an anterior segment image, which have been captured by an imaging optical system.
Figure 4:
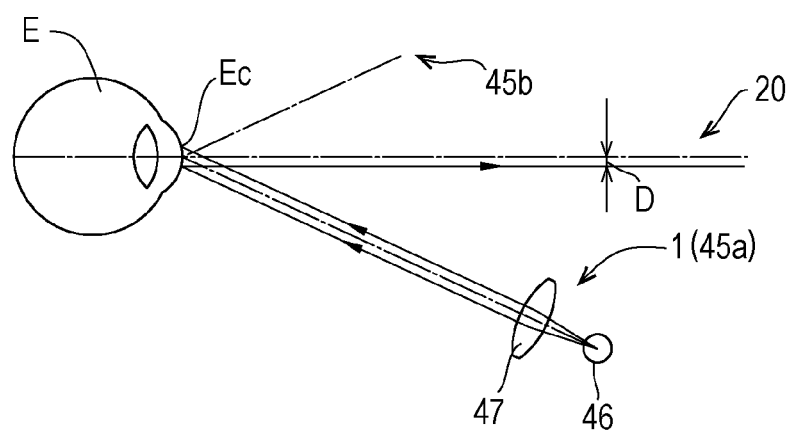
FIG. 4 is a diagram illustrating a method for measuring a corneal shape using a first target pattern image.

The invention claimed is:

1. A cornea shape measurement apparatus for measuring a corneal shape of an examinee's eye, comprising:
a first projecting optical system configured to project a first target on the cornea;
a first imaging optical system configured to capture a reflection image of the first target projected on the cornea;
a second projecting optical system configured to project a second target different from the first target on the cornea to measure the corneal shape;
a second imaging optical system configured to capture a reflection image of the second target projected on the cornea; and
a calculation controller configured to measure a first corneal shape of the examinee's eye based on the reflection image of the first target, the reflection image having been captured by the first imaging optical system, adjust the amount of projection light of the second projecting optical system based on the first corneal shape, and measure a second corneal shape of the examinee's eye based on the reflection image of the second target, the reflection image having been captured by the second imaging optical system,
wherein the calculation controller measures a radius of curvature of the cornea based on the reflection image of the first target, the reflection image having been captured by the first imaging optical system, sets the amount of projection light of the second projecting optical system smaller as the radius of curvature is larger, and sets the amount of projection light of the second projecting optical system larger as the radius of curvature is smaller.

2. The cornea shape measurement apparatus according to claim 1, wherein
the first projecting optical system includes an infrared light source, and projects the first target on the cornea with infrared light, and
the second projecting optical system includes a visible light source, and projects the second target on the cornea with visible light.

3. The cornea shape measurement apparatus according to claim 1, wherein the second projecting optical system projects a target having a wider projection area on the cornea than the first target, as the second target on the cornea.

4. The cornea shape measurement apparatus according to claim 2, wherein the second projecting optical system projects a target having a wider projection area on the cornea than the first target, as the second target on the cornea.

5. The cornea shape measurement apparatus according to claim 1, wherein the first imaging optical system serves also as the second imaging optical system.

6. The cornea shape measurement apparatus according to claim 2, wherein the first imaging optical system serves also as the second imaging optical system.

7. The cornea shape measurement apparatus according to claim 3, wherein the first imaging optical system serves also as the second imaging optical system.

8. The cornea shape measurement apparatus according to claim 4, wherein the first imaging optical system serves also as the second imaging optical system.

9. The cornea shape measurement apparatus according to claim 1, wherein the calculation controller determines whether or not the first corneal shape satisfies a predetermined threshold, and controls the amount of projection light of the second projection optical system based on the determined result.

10. The cornea shape measurement apparatus according to claim 1, the cornea shape measurement apparatus further comprising a third projecting optical system configured to project a third target on the cornea from a front direction of the cornea, wherein
the first projecting optical system is configured to project the first target on the cornea in an oblique direction with respect to the cornea.

11. A cornea shape measurement apparatus for measuring a corneal shape of an examinee's eye, comprising:
a first projecting optical system configured to project a first target on the cornea;
a first imaging optical system configured to capture a reflection image of the first target projected on the cornea;
a second projecting optical system configured to project a second target different from the first target on the cornea to measure the corneal shape;
a second imaging optical system configured to capture a reflection image of the second target projected on the cornea;
a third projecting optical system configured to project a third target on the cornea from a front direction of the cornea; and
a calculation controller configured to measure a first corneal shape of the examinee's eye based on the reflection image of the first target, the reflection image having been captured by the first imaging optical system, adjust the amount of projection light of the second projecting optical system based on the first corneal shape, and measure a second corneal shape of the examinee's eye based on the reflection image of the second target, the reflection image having been captured by the second imaging optical system, wherein
the first projecting optical system is configured to project the first target on the cornea in an oblique direction with respect to the cornea; and
the calculation controller
determines a distance between the first target and the third target as an image height,
measures a radius of curvature of the cornea based on the image height,
determines whether or not the radius of curvature is larger than a predetermined threshold,
adjusts the amount of projection light at a first light amount level if the radius of curvature is larger than the predetermined threshold, and
adjusts the amount of projection light at a second light amount level if the radius of curvature is equal to or less than the predetermined threshold, the second light amount level being larger than the first light amount level.

12. A cornea shape measurement apparatus for measuring a corneal shape of an examinee's eye, comprising:
a first projecting optical system configured to project a first target on the cornea;
a first imaging optical system configured to capture a reflection image of the first target projected on the cornea;
a second projecting optical system configured to project a second target different from the first target on the cornea to measure the corneal shape;
a second imaging optical system configured to capture a reflection image of the second target projected on the cornea;
a third projecting optical system configured to project a third target on the cornea from a front direction of the cornea; and
a calculation controller configured to measure a first corneal shape of the examinee's eye based on the reflection image of the first target, the reflection image having been captured by the first imaging optical system, adjust the amount of projection light of the second projecting optical system based on the first corneal shape, and measure a second corneal shape of the examinee's eye based on the reflection image of the second target, the reflection image having been captured by the second imaging optical system, wherein
the first projecting optical system is configured to project the first target on the cornea in an oblique direction with respect to the cornea; and
the calculation controller
determines a distance between the first target and an imaging optical axis of the third projecting optical system as an image height,
measures a radius of curvature of the cornea based on the image height,
determines whether or not the radius of curvature is larger than a predetermined threshold,
adjusts the amount of projection light at a first light amount level if the radius of curvature is larger than the predetermined threshold, and
adjusts the amount of projection light at a second light amount level if the radius of curvature is equal to or less than the predetermined threshold, the second light amount level being larger than the first light amount level.

* * * * *